(12) United States Patent
Lin et al.

(10) Patent No.: US 10,435,395 B1
(45) Date of Patent: Oct. 8, 2019

(54) CRYSTAL FORMS OF LIFITEGRAST

(71) Applicant: ScinoPharm Taiwan, Ltd., Shan-Hua, Tainan (TW)

(72) Inventors: Wen-Wei Lin, Tainan (TW); Tsung-Cheng Hu, Tainan (TW); YuanChang Huang, Tainan (TW); Ming-Chih Wu, Tainan (TW)

(73) Assignee: SCINOPHARM TAIWAN, LTD., Shan-Hua, Tainan (TW)

( * ) Notice: Subject to any disclaimer, the term of this patent is extended or adjusted under 35 U.S.C. 154(b) by 0 days.

(21) Appl. No.: 16/296,354

(22) Filed: Mar. 8, 2019

Related U.S. Application Data

(60) Provisional application No. 62/650,502, filed on Mar. 30, 2018.

(51) Int. Cl.
*C07D 405/06* (2006.01)

(52) U.S. Cl.
CPC ........ *C07D 405/06* (2013.01); *C07B 2200/13* (2013.01)

(58) Field of Classification Search
CPC ..................................................... C07D 405/06
USPC ......................................................... 546/146
See application file for complete search history.

(56) References Cited

U.S. PATENT DOCUMENTS 8,367,701 B2  2/2013  Burnier et al.
2015/0336939 A1  11/2015  Zeller et al.

*Primary Examiner* — Patricia L Morris
(74) *Attorney, Agent, or Firm* — Enshan Hong; VLP Law Group LLP

(57) ABSTRACT

Crystalline form S1 of lifitegrast characterized by a powder X-ray diffraction pattern with peaks at about 10.7±0.2, 16.2±0.2, 19.9±0.2, 22.1±0.2, 24.7±0.2, and 25.9±0.2 degrees two-theta, crystalline form S2 of lifitegrast characterized by a powder X-ray diffraction pattern with peaks at about 16.4±0.2, 24.9±0.2, and 26.2±0.2 degrees two-theta, and processes of making thereof are provided.

8 Claims, 6 Drawing Sheets

CRYSTAL FORMS OF LIFITEGRAST

CROSS-REFERENCES TO RELATED APPLICATIONS

This application claims priority from U.S. Provisional Patent Application Ser. No. 62/650,502, which was filed on Mar. 30, 2018. The entire content of this provisional application is incorporated herein by reference.

BACKGROUND OF THE INVENTION

The present application relates to crystalline forms of lifitegrast that are useful for the development and optimization of a pharmaceutical composition containing lifitegrast.

The chemical name for lifitegrast is (S)-2-(2-(benzofuran-6-carbonyl)-5,7-dichloro-1,2,3,4-tetrahydroisoquinoline-6carboxamido)-3-(3-(methylsulfonyl)phenyl)propanoic acid. The molecular formula of lifitegrast is $C_{29}H_{24}C_{12}N_2O_7S$ and its molecular weight is 615.5. The strucgtural formula of lifitegrast is:

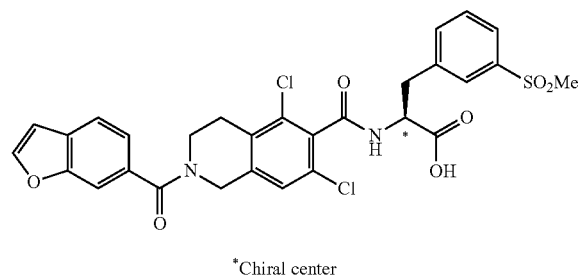 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

*Chiral center

Xiidra (lifitegrast ophthalmic solution) 5% is a lymphocyte function-associated antigen-1 (LFA-1) antagonist indicated for the treatment of the signs and symptoms of dry eye disease (DED).

U.S. Pat. No. 8,367,701B2 and U.S. Patent Application Publication No. 2015/0336939A1 disclose six crystalline forms of lifitegrast. These crystalline forms have their inevitable shortcoming. For example, these crystalline forms are not easy to prepare.

Therefore, there remains a need for the development of improved form of lifitegras.

SUMMARY OF THE INVENTION

The first aspect of the present invention is a crystalline form of lifitegrast (hereafter designated as crystalline form S1) characterized by a powder X-ray diffraction ("PXRD") pattern with peaks at about 10.7, 16.2, 19.9, 22.1, 24.7 and 25.9±0.2 degrees two-theta.

Preferably, the crystalline form S1 is further characterized by a powder X-ray diffraction pattern with peaks at about 14.9, 15.3, 15.7, 17.5, 23.4 and 29.2±0.2 degrees two-theta.

More preferably, the crystalline form S1 is further characterized by a powder X-ray diffraction pattern with peaks at about 12.5, 13.2, 14.3 and 22.7±0.2 degrees two-theta.

The crystalline form S1 is preferably characterized by a powder X-ray diffraction pattern as substantially depicted in FIG. 1.

The crystalline form S1 may be further characterized by thermal gravimetric analysis ("TGA"). In TGA thermogram FIG. 2, a weight loss step is observed with temperature increased, and LOD at 160° C. is about 5.3%.

The crystalline form S1 may be further characterized by Differential Scanning Calorimetric ("DSC"). In DSC thermogram FIG. 3, an endothermic peak occurs with maximum temperature at 31.5° C., and an endothermic peak occurs with onset temperature at 134.8° C.

The crystalline form S1 of lifitegrast may be prepared by dissolving lifitegrast in methanol and then adding n-heptane to form a slurry comprising a precipitate; isolating the precipitate; and drying the precipitate to obtain the crystalline form S1 of lifitegrast.

In the alternative, the crystalline form S1 of lifitegrast may be prepared by mixing lifitegrast with methanol to form a slurry comprising a precipitate; isolating the precipitate; and drying the precipitate to obtain the crystalline form S1 of lifitegrast. For example, lifitegrast may first be dissolved in methanol at 20-30° C., then a little gel is formed on the bottom of flask. The gel-like lifitegrast may serve as seed and induce a slurry generation.

The second aspect of the present invention is a crystalline lifitegrast (hereafter designated as crystalline form S2) characterized by a powder X-ray diffraction ("PXRD") pattern with peaks at about 16.4, 24.9 and 26.2±0.2 degrees two-theta.

Preferably, the crystalline form S2 is further characterized by a powder X-ray diffraction pattern with peaks at about 8.2, 10.8, 13.3, 17.7, 19.8 and 22.4±0.2 degrees two-theta.

More preferably, the crystalline form S1 is further characterized by a powder X-ray diffraction pattern with peaks at about 12.6, 14.4, 14.6, 15.4, 15.8 and 23.4±0.2 degrees two-theta.

The crystalline form S2 is preferably characterized by a powder X-ray diffraction pattern as substantially depicted in FIG. 4.

The crystalline form S2 may be further characterized by thermal gravimetric analysis ("TGA"). In TGA thermogram FIG. 5, a weight loss step is observed with temperature increased, and LOD at 150° C. is 3.4%.

The crystalline form S2 may be further characterized by Differential Scanning Calorimetric (DSC). In DSC thermogram FIG. 6, an endothermic peak occurs with maximum temperature at 34.3° C., and an endothermic peak occurs with onset temperature at 81.1° C.

The crystalline form S2 of lifitegrast may be prepared by suspending a crystalline form S1 of lifitegrast in water to obtain a suspension comprising a precipitate; isolating the precipitate; and drying the precipitate to obtain the crystalline form S2 of lifitegrast.

In the alternative, the crystalline form S2 of lifitegrast may be prepared by drying a crystalline form S1 of lifitegrast in the presence of water moisture in the environement to obtain the crystalline form S2 of lifitegrast. For example, water may be pourted into a beaker and transferred to oven to lead a humid environment.

Compared to the forms reported in the art, the crystalline forms of lifitegrast in accordance with the present invention are stable, have a good crystallinity, and do not convert to other known crystalline forms easily in the preparation of lifitegrast on large scale. In addition, the processes for preparing the crystalline forms of lifitegrast according to the present inveiton are conducted under mild reaction conditions and very easy to practice. The processes in accordance with the present inveiton provide crystalline forms of lifitegrast at high yields and are suitable for the manufacture of lifitegrast on large scale.

DETAILED DESCRIPTION OF PREFERRED EMBODIMENTS OF THE INVENTION

The following examples are provided to illustrate, but not to limit, the present invention. Examples described herein comprise a process for preparing crystalline forms of lifitegrast suitable for either laboratory-scale or industrial scale.

EXPERIMENTAL METHODOLOGY

XRD Analysis

X-ray Powder Diffraction patterns were collected on a Bruker AXS D8 diffractometer using Cu Kα1 radiation (40 kV, 40 mA), θ-2θ goniometer, and divergence of V4 and receiving slits, a Ge monochromator and LynxEye detector. The representative XRPD pattern was collected under ambient condition.

The details of the scanning parameters were:
Angular range: 5-40°
Step size: 0.02°
Scan speed: 0.6 sec/step

Thermal Gravimetric Analysis

TGA data was collected on a TA Instrument Q500 TGA. Each sample (15-20 mg) was loaded onto a pre-tared platinum crucible and the balance and furnace were purged with nitrogen prior to the analysis with a flow rate set as 40±5 and 60±5 mL/min, respectively. The heating process was programmed to start from 30° C. and stop at 300° C. with a 10° C./min ramp.

Differential Scanning Calorimetry

DSC data was collected on a TA Instrument MDSC Q200. Each sample (2-5 mg) was loaded onto a hermetic pan and the analysis was carried out under a constant flow of nitrogen (60 mL/min). The heating process was programmed to start from 30° C. and stop at 250° C. with a 10° C./min ramp.

EXAMPLE 1

Figure 1:
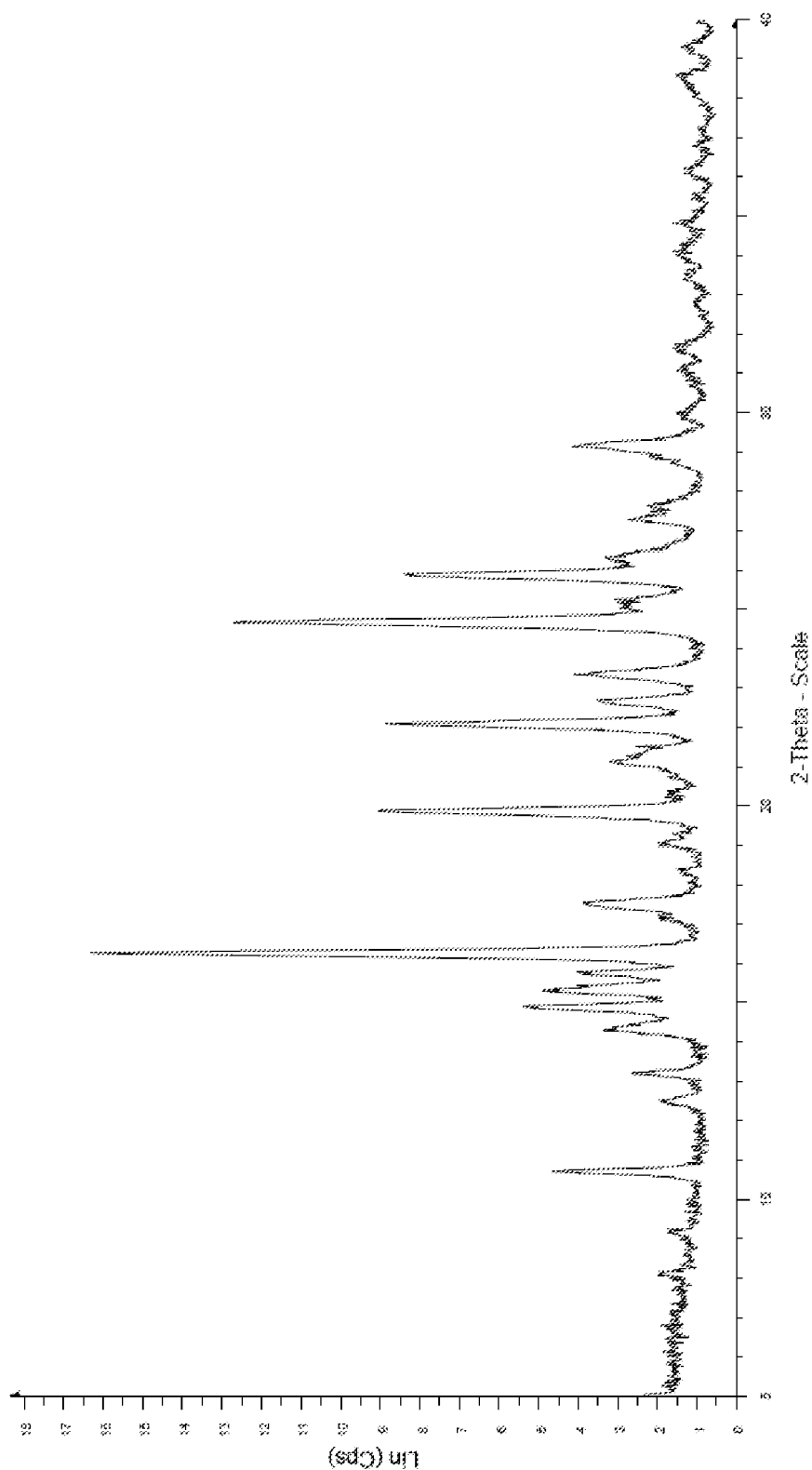
FIG. 1 illustrates a powder X-ray diffraction pattern of crystalline Form S1 lifitegrast characterized by a powder X-ray diffraction pattern.
Figure 2:
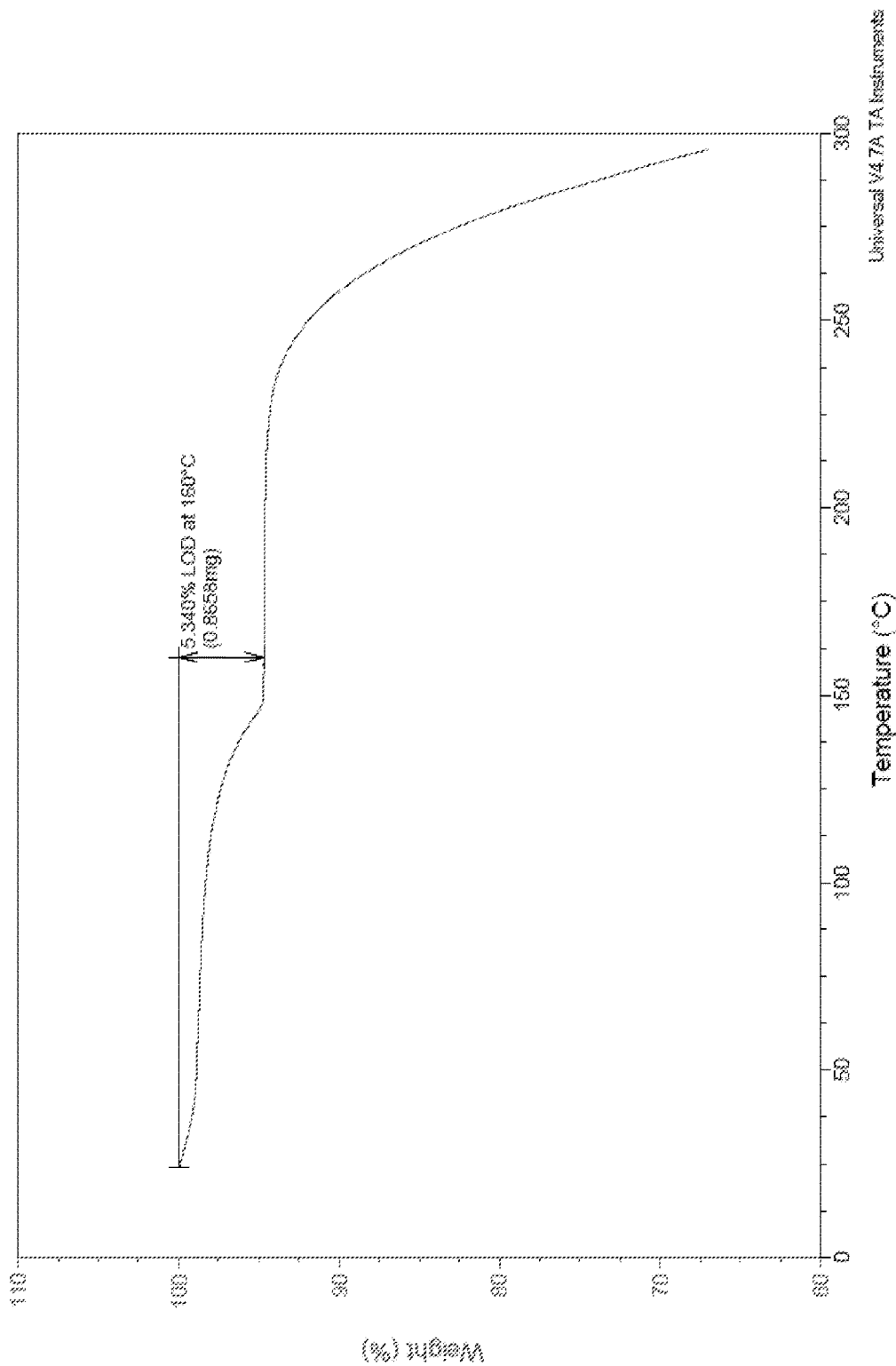
FIG. 2 illustrates a TGA thermogram for crystalline Form S1.
Figure 3:
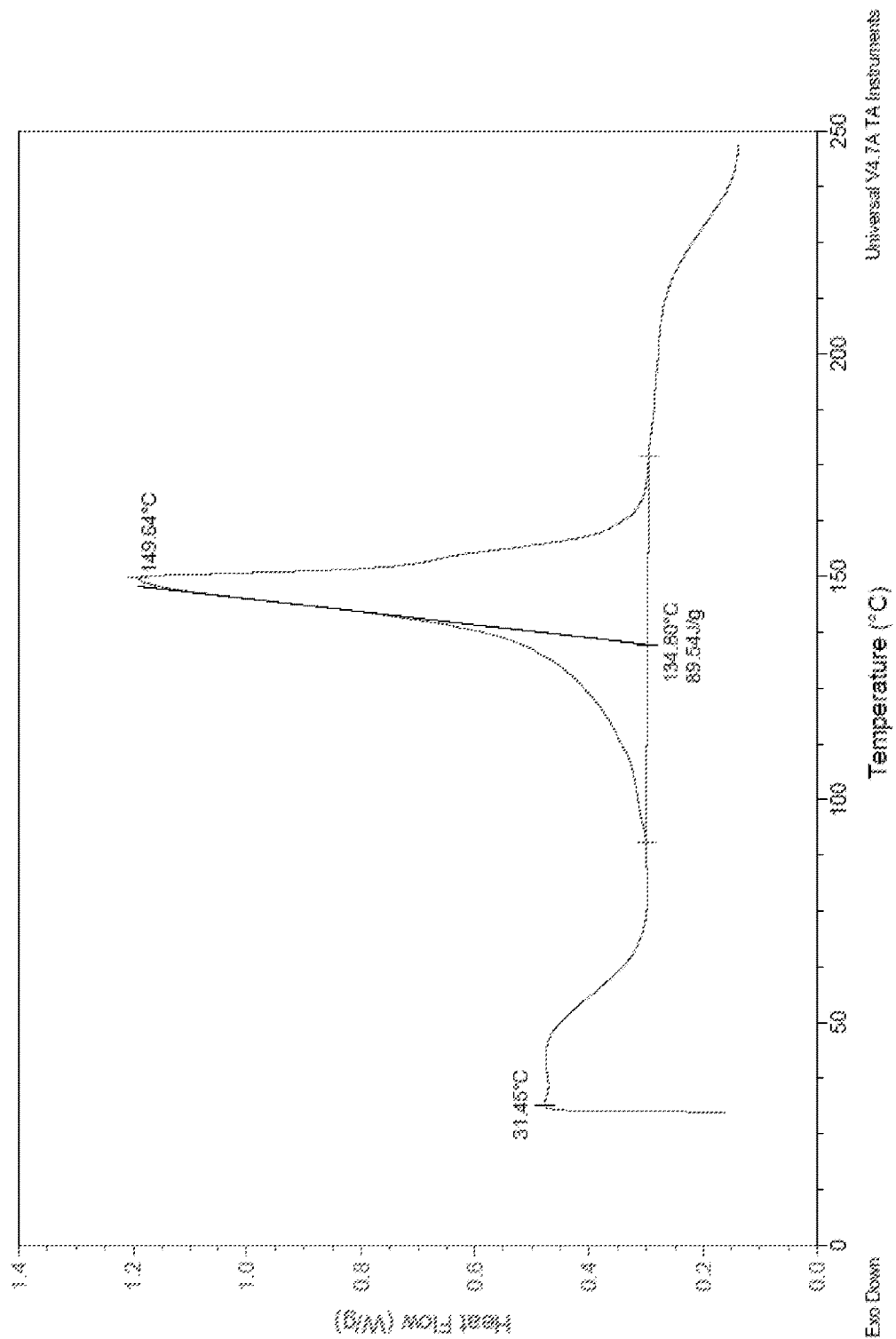
FIG. 3 illustrates a DSC thermogram for crystalline Form S1.

The Preparation of the Crystalline Form S1 of Lifitegrast 0.214 g of lifitegrast was dissolve in 5 mL of methanol at room temperature (about 25-30° C.). The resulting mixture was stirred till complete dissolution. About 10 mL of n-heptane was added at about 7° C., stirred and hold at refrigerator. The suspension solution was filtered to obtain a wet cake. The wet cake was dried by nitrogen purging to provide the crystalline form S1 of lifitegrast. The PXRD pattern of the dried olaparib was measured and and confirmed to have the same pattern as illustrated in FIG. 1. The PXRD characteristics of the crystalline form S1 of lifitegrast are reflected in the following table:

| Angle 2-Theta ° | Intensity Cps | Intensity % % |
|---|---|---|
| 8.1 | 1.92 | 11.8 |
| 9.1 | 1.69 | 10.3 |
| 10.7 | 4.62 | 28.3 |
| 12.5 | 1.83 | 11.2 |
| 13.2 | 2.58 | 15.8 |
| 14.3 | 3.31 | 20.3 |
| 14.9 | 5.37 | 32.8 |
| 15.3 | 4.9 | 30 |
| 15.7 | 3.98 | 24.3 |
| 16.2 | 16.3 | 100 |
| 17.1 | 1.9 | 11.6 |
| 17.5 | 3.83 | 23.4 |
| 18.3 | 1.38 | 8.4 |
| 19 | 1.91 | 11.7 |
| 19.9 | 9.04 | 55.3 |
| 20.3 | 1.69 | 10.3 |
| 21.1 | 3.15 | 19.3 |
| 21.4 | 2.2 | 13.5 |
| 22.1 | 8.87 | 54.3 |
| 22.7 | 3.41 | 20.9 |
| 23.4 | 4.06 | 24.9 |
| 24.7 | 12.7 | 77.7 |
| 25.2 | 2.74 | 16.8 |
| 25.9 | 8.38 | 51.3 |
| 26.3 | 3.27 | 20 |
| 27.3 | 2.7 | 16.5 |
| 27.6 | 2.2 | 13.5 |
| 29.2 | 4.12 | 25.2 |
| 30 | 1.45 | 8.9 |
| 31.1 | 1.32 | 8.1 |
| 31.6 | 1.54 | 9.4 |
| 32.8 | 1 | 6.1 |
| 33.5 | 1.22 | 7.4 |
| 34.1 | 1.47 | 9 |
| 34.8 | 1.55 | 9.5 |
| 35.5 | 0.98 | 6 |
| 36.2 | 1.13 | 6.9 |
| 36.8 | 0.96 | 5.9 |
| 38.6 | 1.48 | 9.1 |
| 39.3 | 1.37 | 8.4 |

EXAMPLE 2

The Preparation of the Crystalline Form S1 of Lifitegrast 5.120 g of lifitegrast was dissolved in 118 mL of methanol and then precipitated at room temperature. The suspension solution was filtered to obtain a wet cake. The wet cake was dried by nitrogen purging and at 60° C. oven drying to provide the crystalline form S1 of lifitegrast. The PXRD pattern of the dried lifitegrast was measured and confirmed to have the same pattern as illustrated in FIG. 1.

EXAMPLE 3

The Preparation of the Crystalline Form S1 of Lifitegrast (2S)-2-amino-3-(3-methylsulfonylphenyl)propanoic acid (SPT1428SM3) (21.54 g, 1.5 equiv), purified process water (PPW) (150 mL), acetonitrile (ACN) (120 mL) and N,N-Diisopropylethylamine (DIPEA) (25.7 mL, 2.5 equiv) were added to a suitable reactor at 20-30° C. The resulting SPT1428SM3 was stirred at 20-30° C. Triazolo[4,5-b]pyridin-3-yl 2-(benzofuran-6-carbonyl)-5,7-dichloro-3,4-dihydro-1H-isoquinoline-6-carboxylate (SPT1428M2) (30.00 g, 1.0 equiv) was added to the above solution at 20-30° C. The resulting slurry was heated to 40-45° C. for NLT (no less than) 4 hr (hours). When the reaction was complete, the resulting solution was filtered and rinsed with PPW (150 mL). The reaction was concentrated to about 330 mL. The resulting solution was cooled to 20-30° C. followed by addition of 2-methyltetrahydrofuran (2-MeTHF) (300 mL). The resulting biphasic solution was then adjusted with 3N HCl to pH of aqueous layer reached 2-3 at 20-30° C. The organic layer was then washed with 10% NaCl (90 mL). The organic layer was added activated charcoal, wet powder (1.50 g) and heated to 40-45° C. for 1 hr. The suspension solution was filtered by a pad of Celite (15.0 g) and washed by 2-MeTHF (120 mL). The filtrate was collected and was concentrated to about 150 mL. The reaction mixture was added MeOH (450 mL) stirred at 40-50° C. for NLT 0.5 hr then cooled to 20-30° C. The resulting slurry was filtered, and the wet cake was washed with MeOH (240 mL). The wet cake was purged under vacuum and nitrogen to provide the crystalline form S1 of lifitegrast.

EXAMPLE 4

Figure 4:
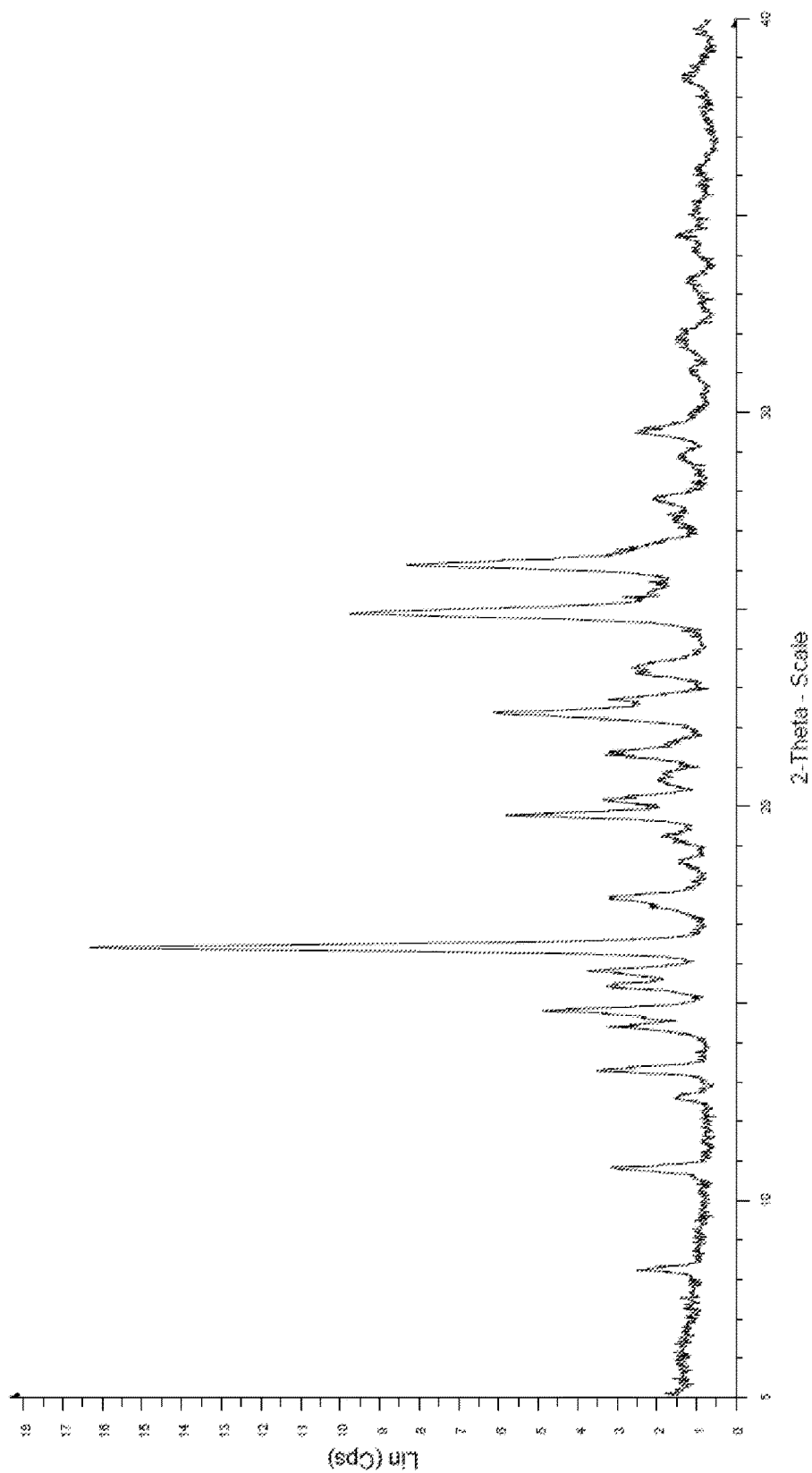
FIG. 4 illustrates a powder X-ray diffraction pattern of crystalline Form S2 lifitegrast characterized by a powder X-ray diffraction pattern.
Figure 5:
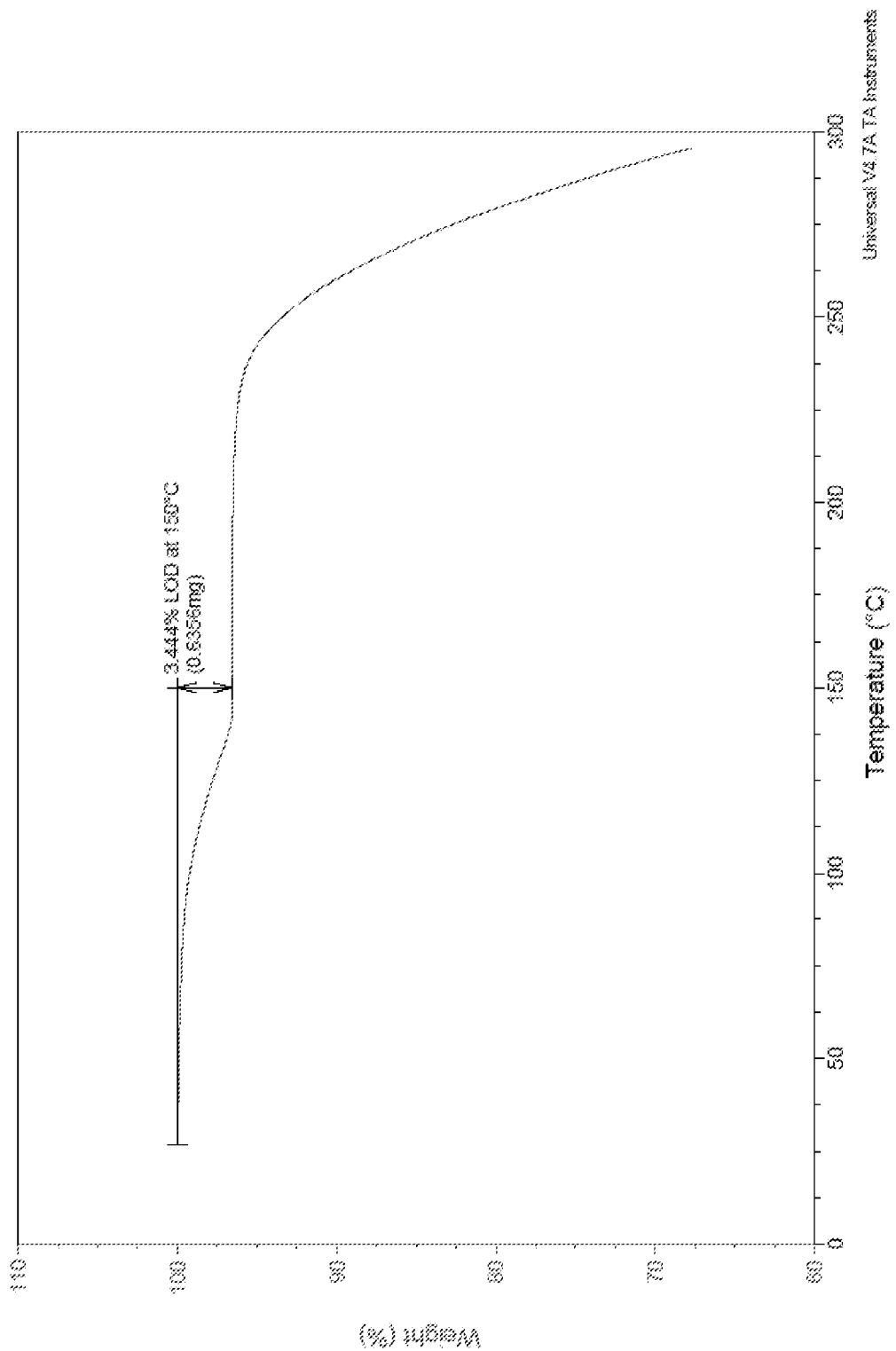
FIG. 5 illustrates a TGA thermogram for crystalline Form S2.
Figure 6:
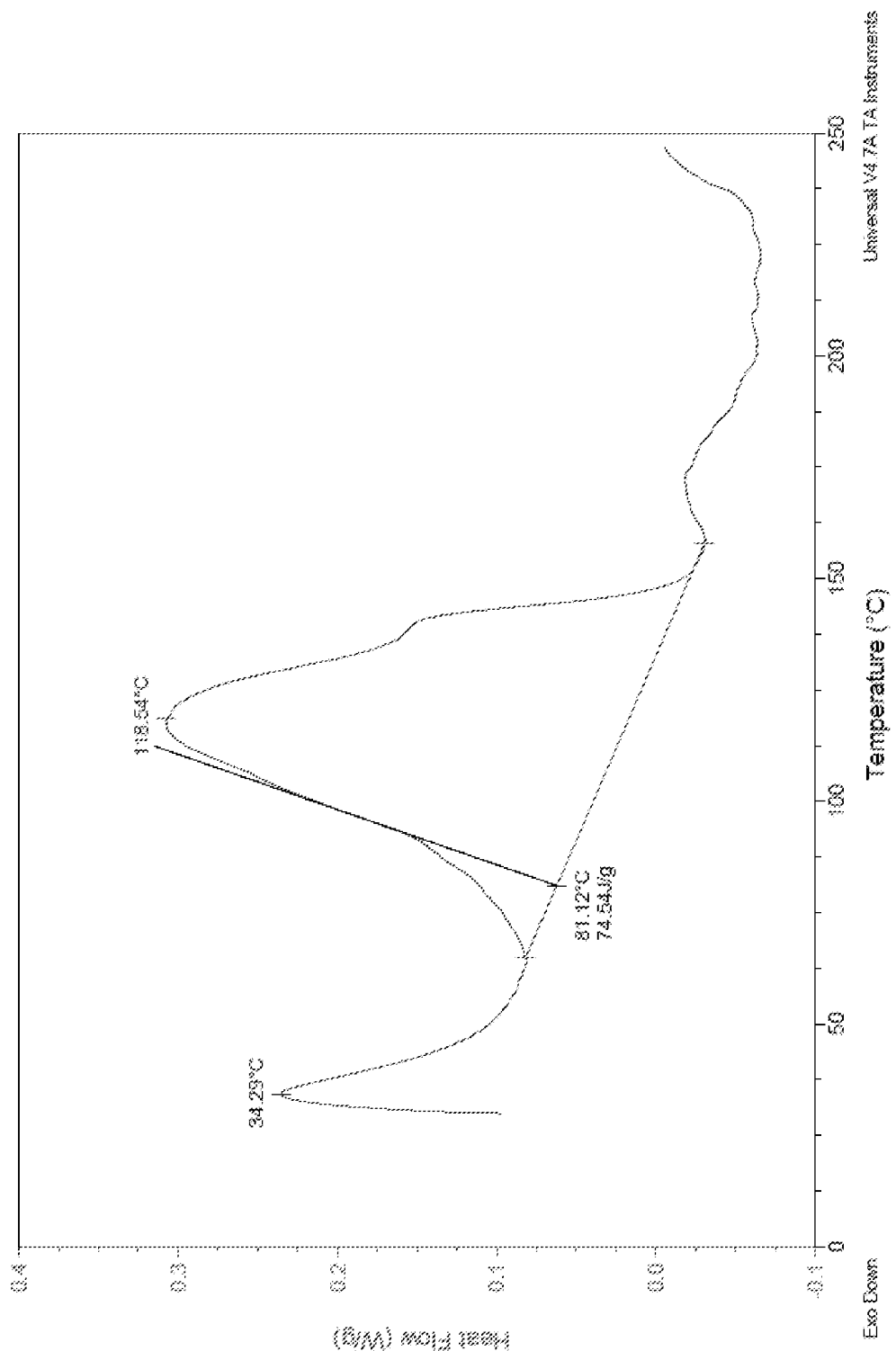
FIG. 6 illustrates a TGA thermogram for crystalline Form S2.

The Preparation of the Crystalline Form S2 of Lifitegrast 0.403 g of lifitegrast was suspended in 16 mL of water at about 60° C. The suspension solution was filtered to obtain a wet cake. The wet cake was dried by nitrogen purging to provide the crystalline form S1 of lifitegrast. The PXRD pattern of the dried lifitegrast was measured and and confirmed to have the same pattern as illustrated in FIG. 4. The PXRD characteristics of the crystalline form S2 of lifitegrast are reflected in the following table:

| Angle 2-Theta ° | Intensity Cps | Intensity % % |
|---|---|---|
| 8.2 | 2.2 | 13.5 |
| 10.8 | 3.02 | 18.5 |
| 12.6 | 1.51 | 9.2 |
| 13.3 | 3.48 | 21.3 |
| 14.4 | 3.2 | 19.6 |
| 14.8 | 4.85 | 29.7 |
| 15.4 | 3.24 | 19.8 |
| 15.8 | 3.71 | 22.7 |
| 16.4 | 16.3 | 100 |
| 17.7 | 3.19 | 19.6 |
| 18.6 | 1.31 | 8 |
| 19.2 | 1.85 | 11.3 |
| 19.8 | 5.8 | 35.5 |
| 20.2 | 3.33 | 20.4 |
| 20.8 | 1.84 | 11.3 |
| 21.4 | 3.17 | 19.4 |
| 22.4 | 6.11 | 37.4 |
| 22.7 | 3.18 | 19.5 |
| 23.4 | 2.47 | 15.1 |
| 24.9 | 9.73 | 59.6 |
| 26.2 | 8.29 | 50.8 |
| 27.3 | 1.55 | 9.5 |
| 27.8 | 2.06 | 12.6 |
| 28.9 | 1.42 | 8.7 |
| 29.5 | 2.43 | 14.9 |

-continued

| Angle 2-Theta ° | Intensity Cps | Intensity % % |
|---|---|---|
| 31.1 | 1.12 | 6.8 |
| 31.9 | 1.46 | 9 |
| 33.4 | 1.13 | 6.9 |
| 34.1 | 0.98 | 6 |
| 34.5 | 1.49 | 9.2 |
| 36.2 | 0.99 | 6.1 |
| 38.5 | 1.29 | 7.9 |
| 39.8 | 1.02 | 6.3 |

EXAMPLE 5

The Preparation of the Crystalline Form S2 of Lifitegrast 0.637 g of lifitegrast was dried by oven drying with water moisture at 60° C. to provide the crystalline form S2 of lifitegrast. The PXRD pattern of the dried olaparib was measured and confirmed to have the same pattern as illustrated in FIG. 4.

What is claimed is:

1. Crystalline form S1 of lifitegrast characterized by a powder X-ray diffraction pattern with peaks at about 10.7±0.2, 16.2±0.2, 19.9±0.2, 22.1±0.2, 24.7±0.2, and 25.9±0.2 degrees two-theta.

2. The crystalline form S1 of lifitegrast of claim 1 further characterized by a powder X-ray diffraction pattern with peaks at about 14.9±0.2, 15.3±0.2, 15.7±0.2, 17.5±0.2, 23.4±0.2, and 29.2±0.2 degrees two-theta.

3. The crystalline form S1 of lifitegrast of claim 1 further characterized by a powder X-ray diffraction pattern with peaks at about 12.5±0.2, 13.2±0.2, 14.3±0.2, and 22.7±0.2 degrees two-theta.

4. The crystalline form S1 of lifitegrast of claim 1 further characterized by a powder X-ray diffraction pattern as substantially depicted in FIG. 1.

5. The crystalline form S1 of lifitegrast of claim 1 further characterized by a weight loss of about 5.3% at a temperature up to 160° C., as measured by thermal gravimetric analysis (TGA), an endothermic peak occurring with maximum temperature at 31.5° C., and an endothermic peak occurring with onset temperature at 134.8° C., as measured by Differential Scanning Calorimetric (DSC).

6. The crystalline form S1 of lifitegrast of claim 1, wherein the crystalline form S1 of lifitegrast is a methanol solvate.

7. A process of making the crystalline form S1 of claim 1 comprising dissolving crude solid lifitegrast in methanol to form a solution, and then adding n-heptane to the solution to form a slurry comprising a precipitate; isolating the precipitate; and drying the precipitate to obtain the crystalline form S1 of lifitegrast.

8. A process of making the crystalline form S1 of claim 1 comprising mixing crude solid lifitegrast with methanol to form a slurry comprising a precipitate; isolating the precipitate; and drying the precipitate to obtain the crystalline form S1 of lifitegrast.

* * * * *